United States Patent
Huang et al.

(10) Patent No.: US 12,268,515 B1
(45) Date of Patent: Apr. 8, 2025

(54) MULTI-DIMENSIONAL BROAD-SPECTRUM CLINICAL IN-SITU TESTING EQUIPMENT FOR EVALUATING MECHANICAL PROPERTIES OF PLANTAR SOFT TISSUE

(71) Applicant: Fudan University, Shanghai (CN)

(72) Inventors: Ran Huang, Shanghai (CN); Longyan Wu, Shanghai (CN); Jun Zhu, Shanghai (CN); Lisheng Tang, Shanghai (CN); Xinyi Ning, Shanghai (CN); Xin Ma, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 18/772,135

(22) Filed: Jul. 13, 2024

(30) Foreign Application Priority Data

Jan. 30, 2024 (CN) .......................... 202410122180.4

(51) Int. Cl.
*A61B 5/00* (2006.01)
(52) U.S. Cl.
CPC .......... *A61B 5/4533* (2013.01); *A61B 5/0053* (2013.01); *A61B 5/0057* (2013.01)
(58) Field of Classification Search
CPC .... A61B 5/4533; A61B 5/0053; A61B 5/0057
See application file for complete search history.

(56) References Cited

U.S. PATENT DOCUMENTS

| | | | | |
|---|---|---|---|---|
| 5,989,199 | A * | 11/1999 | Cundari | A61B 5/0053 |
| | | | | 600/595 |
| 7,926,363 | B2 * | 4/2011 | Miller | A43B 13/38 |
| | | | | 73/862.041 |

(Continued)

FOREIGN PATENT DOCUMENTS

| | | | | |
|---|---|---|---|---|
| CN | 109498043 A | * | 3/2019 | ........... A61B 5/0053 |
| CN | 115500814 A | * | 12/2022 | ........... A61B 5/0048 |
| CN | 117664705 A | * | 3/2024 | |

OTHER PUBLICATIONS

CNIPA, Notification of a First Office Action for CN202410122180. 4, Mar. 13, 2024.

(Continued)

*Primary Examiner* — Sean P Dougherty (74) *Attorney, Agent, or Firm* — Hemisphere Law, PLLC; Zhigang Ma (57) ABSTRACT

The invention provides a multi-dimensional broad-spectrum clinical in-situ testing equipment designed to evaluate the material properties of plantar soft tissue. The equipment comprises the following features: 1. A testing table with a designated area corresponding to the sole of the foot; 2. A vertical reciprocating stress-strain testing unit mounted on the testing table, for applying vertical tensile and compressive stresses to the plantar and measuring the stress-strain responses; 3. A shear stress-strain testing unit, mounted on the testing table, for applying shear stresses to the plantar and measuring the stress-strain responses; 4. A torque stress-strain detection unit, positioned on the testing stage, for applying torque to the plantar and measuring the stress-strain responses; 5. A lifting mechanism that facilitates the vertical movement of the three testing units. In conclusion, the device is capable of multi-dimensional detection of the mechanical properties of plantar and features a compact structure and easy portability.

3 Claims, 5 Drawing Sheets

(56) References Cited

U.S. PATENT DOCUMENTS

| | | | |
|---|---|---|---|
| 2013/0123610 A1* | 5/2013 | Stebbins | A61B 5/0053 |
| | | | 600/421 |
| 2017/0055836 A1* | 3/2017 | Thelen | A61B 5/4533 |
| 2018/0116523 A1* | 5/2018 | Chatzistergos | A61B 5/1036 |
| 2024/0023829 A1* | 1/2024 | Morgan | A61B 5/4528 |
| 2024/0268686 A1* | 8/2024 | Ferraresi | A61B 5/022 |

OTHER PUBLICATIONS

Fudan University (Applicant), Replacement claims (allowed) of CN202410122180.4, Mar. 22, 2024.
CNIPA, Notification to grant patent right for invention in CN202410122180.4, Apr. 3, 2024.

* cited by examiner

MULTI-DIMENSIONAL BROAD-SPECTRUM CLINICAL IN-SITU TESTING EQUIPMENT FOR EVALUATING MECHANICAL PROPERTIES OF PLANTAR SOFT TISSUE

CROSS REFERENCE TO RELATED APPLICATION

This application claims the priority of Chinese Patent Application No. 202410122180.4, entitled "Multi-Dimensional Broad-Spectrum Clinical In-Situ Testing Equipment for Evaluating the Mechanical Properties of Plantar Soft Tissue", filed on Jan. 30, 2024, the disclosure of which is incorporated herein by reference in its entirety.

BACKGROUND OF THE INVENTION

1. Field of the Invention

The present invention relates to the fields of clinical medicine and biomedical engineering, specifically to a multi-dimensional broad-spectrum clinical in-situ testing equipment for evaluating the mechanical properties of plantar soft tissue.

2. Description of Related Art

The plantar soft tissue is located between the dermis of the foot's skin and the bones, comprising a composite material made of fat and specific connective tissues. As a result of natural evolutionary selection, this soft tissue, through its complex composition and fine structure, efficiently achieves various precise physiological functions. Therefore, the characterization of the mechanical properties of soft tissue is critical in the fields of clinical medicine and biomedical engineering.

Common methods for testing the mechanical properties of soft tissue involve applying displacement to ex vivo specimen samples under external loads in a materials testing machine. However, it is controversial because the biochemical state and mechanical properties of soft tissue in an inactivated state do not accurately reflect the true state in vivo. Based on non-invasive requirements, measurement methods for in vivo soft tissue primarily rely on indirect methods such as imaging. However, imaging methods involve radiation hazards, necessitating strict limitations on the number and duration of measurements, and the resulting discrete data are difficult to process mathematically.

It is generally believed that soft tissue possesses both elastic and viscous mechanical properties, giving it characteristics of energy absorption, slow rebound, and creep. In classical materials mechanics, viscoelasticity is typically characterized by dynamic mechanical analysis (DMA) to obtain periodic "stress-strain" data. Therefore, continuous and periodic direct measurement is unavoidable in the study of soft tissue viscoelastic properties. However, currently reported DMA tests are conducted on ex vivo cadaver specimens, which have significant limitations. In recent years, some studies have reported single-pulse in vivo indentation tests to obtain force-displacement and stress relaxation curves, but these still differ significantly from the dynamic periodic stress-strain relationships and viscoelastic analysis in DMA methods. Periodic and continuous mechanical property testing of living tissues is an ideal method not yet reported in this field.

In daily activities, the plantar soft tissue is subjected to repeated tensile and compressive forces, shear forces, and torques. For various orthopedic and systemic diseases, it is necessary to study the forces exerted on the plantar in different directions and forms. However, to date, only pressure has been widely reported, with fewer reports on shear and torque.

Additionally, existing testing devices, to meet the requirements of selecting different points on the plantar, have actuating mechanisms mounted on motion modules, which inevitably affect the precision and stability of the equipment. They also have issues of being relatively large and less mobile.

SUMMARY OF THE INVENTION

The present invention aims to address the aforementioned issues by providing a multi-dimensional broad-spectrum clinical in-situ testing equipment for evaluating the mechanical properties of plantar soft tissue.

The present invention provides a multi-dimensional broad-spectrum clinical in-situ testing equipment for evaluating the mechanical properties of plantar soft tissue, comprising the following features:

A testing table with a designated testing area corresponding to the sole of the foot;

A vertical reciprocating stress-strain testing unit mounted on the testing table, used to apply vertical tensile and compressive stresses to the plantar soft tissues and measure the corresponding stress-strain responses;

A shear stress-strain testing unit, also mounted on the testing table, used to apply transverse shear stresses to the plantar soft tissues and measure the stress-strain responses;

A torque stress-strain detection unit, positioned on the testing stage, used to apply torque to the plantar soft tissues and measure the resulting stress-strain responses;

A lifting mechanism that facilitates the vertical movement of the vertical reciprocating stress-strain detection unit, the shear stress-strain detection unit, and the torque stress-strain detection unit;

The vertical reciprocating stress-strain testing unit, the shear stress-strain testing unit, and the torque stress-strain testing unit are arranged to face each other. Each of the vertical reciprocating stress-strain testing unit, the shear stress-strain testing unit, and the torque stress-strain testing unit includes a detection head, and the three detection heads are distributed at equal angular intervals on the same circumference.

In the multi-dimensional broad-spectrum clinical in-situ testing equipment for evaluating the mechanical properties of plantar soft tissue provided by the present invention, the following features can also be included:

The vertical reciprocating stress-strain testing unit comprises a first driving motor, a first rotary-to-linear motion mechanism, and a first detection probe, as well as a first tension-compression sensor and a first displacement sensor. The first rotary-to-linear motion mechanism is used to convert the rotational motion output by the first driving motor into vertical linear reciprocating motion to drive the first detection probe. The first detection probe serves as the detection head of the vertical reciprocating stress-strain testing unit, which is used to connect with the plantar soft tissue. The first tension-compression sensor is used to detect the pressure exerted by the plantar soft tissue on the first detection probe in the vertical direction, and the first displacement sensor is used to detect the displacement of the first detection probe during the testing process.

The first rotary-to-linear motion mechanism includes a first eccentric wheel, a first connecting rod, a first optical axis, a first linear bearing, a second linear bearing, and a first support frame. The rotational center axis of the first eccentric wheel is connected to the output shaft of the horizontally arranged first driving motor, and the eccentric axis of the first eccentric wheel is connected to the horizontally arranged first connecting rod. The first optical axis is connected to the first connecting rod. The first linear bearing and the second linear bearing are respectively sleeved on both ends of the first optical axis, and the first linear bearing is connected to the first support frame. The first detection probe is arranged at the upper end of the first optical axis. The first tension-compression sensor is connected between the first detection probe and the first optical axis. The first displacement sensor is installed on the first support frame and arranged beside the first optical axis.

The shear stress-strain testing unit comprises a second driving motor, a second rotary-to-linear motion mechanism, and a second detection probe, as well as a second tension-compression sensor, a third tension-compression sensor, and a second displacement sensor. The second rotary-to-linear motion mechanism is used to convert the rotational motion output by the second driving motor into horizontal linear reciprocating motion to drive the second detection probe. The second detection probe serves as the detection head of the shear stress-strain testing unit, which is used to connect with the plantar soft tissue. The second tension-compression sensor is used to detect the pressure exerted by the plantar soft tissue on the second detection probe in the transverse shear direction. The third tension-compression sensor is used to detect the pressure exerted by the plantar soft tissue on the second detection probe in the vertical direction. The second displacement sensor is used to detect the displacement of the second detection probe during the testing process.

The second rotary-to-linear motion mechanism includes a second eccentric wheel, a connecting shaft, a second linear guide rail, a third linear guide rail, an L-shaped plate, and a first square connecting piece. The center of the second eccentric wheel is connected to the output shaft of the vertically arranged second driving motor. One end of the connecting shaft is fixed to the edge of the second eccentric wheel, and the other end is connected to the slider of the second linear guide rail. One end of the second tension-compression sensor is connected to the slider of the second linear guide rail through the L-shaped plate, and the other end is connected to the side of the first square connecting piece. The second detection probe, the third tension-compression sensor, the first square connecting piece, and the slider of the third linear guide rail are connected sequentially. The second displacement sensor is arranged beside the slider of the second linear guide rail.

The torque stress-strain detection unit comprises a third driving motor, a rotary-to-torsion motion mechanism, and a third detection probe, as well as a torque sensor, an angle sensor, and a fourth tension-compression sensor. The rotary-to-torsion motion mechanism is used to convert the rotational motion output by the third driving motor into horizontal torsional reciprocating motion to drive the third detection probe. The third detection probe serves as the detection head of the torque stress-strain detection unit, which is used to connect with the plantar soft tissue to be tested. The torque sensor is used to detect the torque exerted by the plantar soft tissue on the third detection probe. The angle sensor is used to detect the rotation angle of the third detection probe during the testing process. The fourth tension-compression sensor is used to detect the pressure exerted by the plantar soft tissue on the third detection probe in the vertical direction.

The rotary-to-torsion motion mechanism includes an eccentric turntable, a fourth linear guide rail, a first pulley, a second pulley, a synchronous belt, a torsion spline, and a torsion coupling. The center of the eccentric turntable is connected to the output shaft of the vertically arranged third driving motor. The slider of the fourth linear guide rail is installed on the edge of the eccentric turntable. The guide rail of the fourth linear guide rail is arranged horizontally and connected to one end of the vertically arranged torque sensor. The other end of the torque sensor is connected to the first pulley. The first pulley is connected to the second pulley through the synchronous belt. The second pulley is sleeved on the torsion spline. The third detection probe, the torsion spline, the torsion coupling, and the angle sensor are connected sequentially. The fourth tension-compression sensor is arranged directly below the angle sensor.

The testing table includes a fixed plate, damping sheets, and a base plate. The fixed plate is equipped with the vertical reciprocating stress-strain testing unit, the shear stress-strain testing unit, and the torque stress-strain testing unit. The damping sheets are installed between the fixed plate and the base plate.

The lifting mechanism includes a driving component and a Z-axis screw slider module. The vertically arranged driving component is connected to the screw of the Z-axis screw slider module. The slider of the Z-axis screw slider module is connected to and drives the vertical reciprocating stress-strain testing unit, the shear stress-strain testing unit, and the torque stress-strain testing unit to move up and down in the vertical direction.

The diameter of the circumference on which the detection heads are distributed is 10±5 centimeters.

BRIEF DESCRIPTION OF THE DRAWINGS

In order to more clearly illustrate technical solutions of embodiments of the invention or the prior art, drawings will be used in the description of embodiments or the prior art will be given a brief description below. Apparently, the drawings in the following description only are some of embodiments of the invention, the ordinary skill in the art can obtain other drawings according to these illustrated drawings without creative effort.

DESCRIPTION OF REFERENCE NUMERALS

10—Testing table; 11—Support frame; 111—Horizontal beam; 112—Vertical beam; 12—Base plate; 13—Damping sheet; 14—Fixed plate; 15—Top plate; 20—Vertical reciprocating stress-strain testing unit; 21—First driving motor; 22—First rotary-to-linear motion mechanism; 221—First eccentric wheel; 222—First connecting rod; 223—First optical axis; 224—First linear bearing; 225—Second linear bearing; 226—First support frame; 23—First detection probe; 24—First tension-compression sensor; 25—First displacement sensor; 30—Shear stress-strain testing unit; 31—Second driving motor; 32—Second rotary-to-linear motion mechanism; 321—Second eccentric wheel; 322—Connecting shaft; 323—Second linear guide rail; 324—Third linear guide rail; 325—L-shaped plate; 326—First square connecting piece; 33—Second detection probe; 34—Second tension-compression sensor; 35—Third tension-compression sensor; 36—Second displacement sensor; 37—Second support frame; 38—Fixed guide rail; 39—Vertical fixed plate; 40—Torque stress-strain testing unit; 41—Third driving motor; 42—Rotary-to-torsion motion mechanism; 421—Eccentric turntable; 422—Fourth linear guide rail; 423—First pulley; 424—Second pulley; 425—Synchronous belt; 426—Torsion spline; 427—Torsion coupling; 428—Fourth support frame; 429—L-shaped fixing piece; 420—Second square connecting piece; 43—Third detection probe; 44—Torque sensor; 45—Angle sensor; 46—Fourth tension-compression sensor; 47—Third support frame; 50—Lifting mechanism; 51—Driving component; 52—Z-axis screw slider module; 53—Fixing piece.

DETAILED DESCRIPTION OF THE PREFERRED EMBODIMENTS

To facilitate understanding of the technical means, creation characteristics, objectives, and effects of the present invention, the following embodiments are described in conjunction with the accompanying drawings, detailing the multi-dimensional broad-spectrum clinical in-situ testing equipment for evaluating the mechanical properties of plantar soft tissue.

Figure 1:
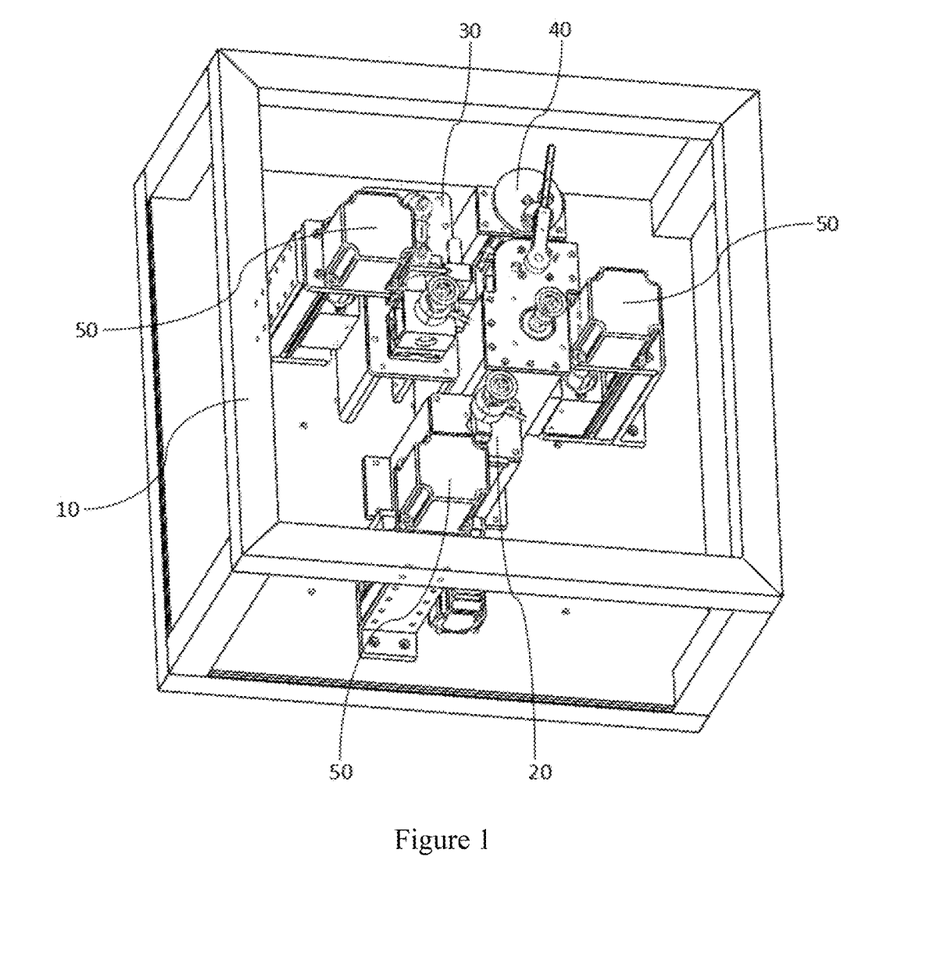
FIG. 1 is a perspective view of the multi-dimensional broad-spectrum clinical in-situ testing equipment for evaluating the mechanical properties of plantar soft tissue according to an embodiment of the present invention.

FIG. 1 shows a perspective view of the multi-dimensional broad-spectrum clinical in-situ testing equipment for evaluating the mechanical properties of plantar soft tissue according to an embodiment of the present invention.

As shown in FIG. 1, this embodiment provides a multi-dimensional broad-spectrum clinical in-situ testing equipment 100 for evaluating the mechanical properties of plantar soft tissue, comprising a testing table 10, a vertical reciprocating stress-strain testing unit 20, a shear stress-strain testing unit 30, a torque stress-strain testing unit 40, and a lifting mechanism 50.

Figure 2:
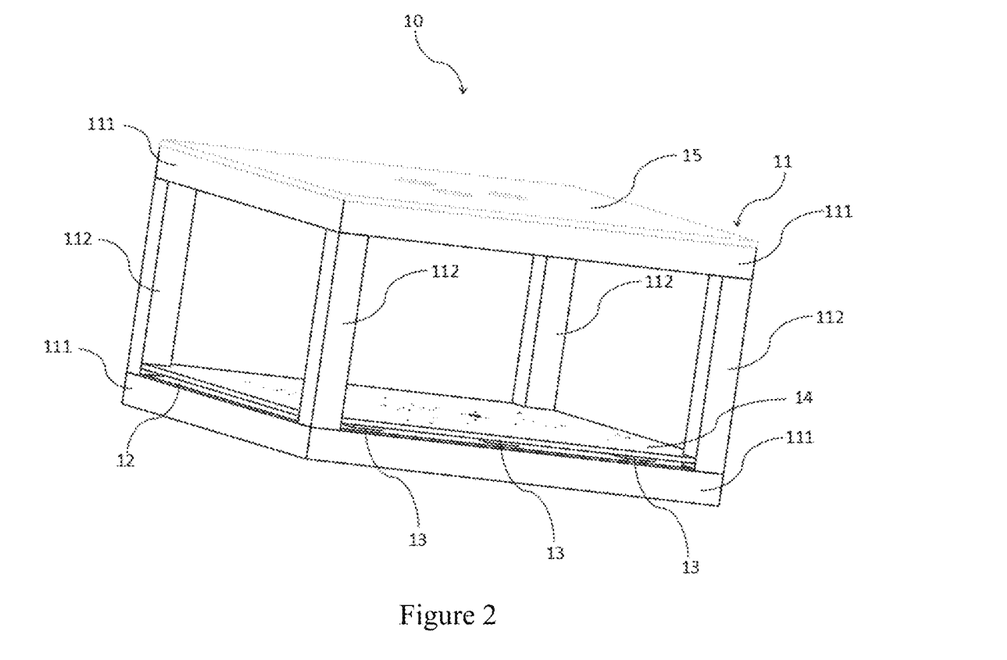
FIG. 2 is a structural diagram of the testing table according to an embodiment of the present invention.

FIG. 2 shows a structural diagram of the testing table according to an embodiment of the present invention.

As shown in FIG. 2, the testing table 10 in this embodiment includes a testing area corresponding to the sole of the foot, which consists of a support frame 11, a base plate 12, damping sheets 13, a fixed plate 14, and a top plate 15.

The support frame 11 includes eight horizontal beams 111 and four vertical beams 112.

The base plate 12 is mounted on the four horizontal beams 111 forming the base of the support frame 11.

The fixed plate 14 is mounted on the base plate 12, and multiple damping sheets 13 are arranged between the fixed plate 14 and the base plate 12 to enhance the stability of the multi-dimensional broad-spectrum clinical in-situ testing equipment 100 for evaluating the mechanical properties of plantar soft tissue.

The top plate 15 is mounted on the four horizontal beams 111 forming the top of the support frame to support the foot.

Figure 3:
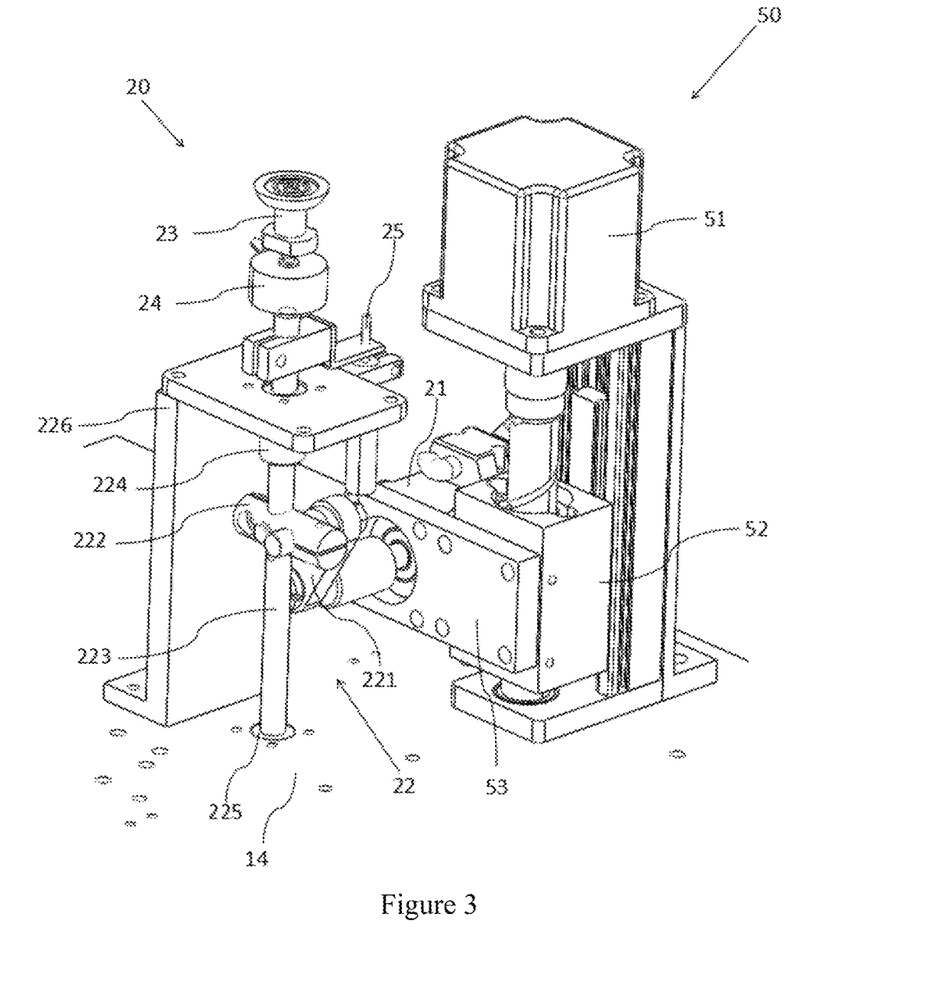
FIG. 3 is a structural diagram of the vertical reciprocating stress-strain testing unit and the corresponding lifting mechanism according to an embodiment of the present invention.

FIG. 3 shows a structural diagram of the vertical reciprocating stress-strain testing unit and the corresponding lifting mechanism according to an embodiment of the present invention.

As shown in FIG. 3, the vertical reciprocating stress-strain testing unit 20 is mounted on the fixed plate 14 of the testing table 10 and is used to apply vertical tensile and compressive stresses to the plantar soft tissues and measure them. It includes a first driving motor 21, a first rotary-to-linear motion mechanism 22, a first detection probe 23, a first tension-compression sensor 24, and a first displacement sensor 25.

The first rotary-to-linear motion mechanism 22 converts the rotational motion output by the first driving motor 21 into vertical linear reciprocating motion to drive the first detection probe 23. It includes a first eccentric wheel 221, a first connecting rod 222, a first optical axis 223, a first linear bearing 224, a second linear bearing 225, and a first support frame 226.

The rotational center axis of the first eccentric wheel 221 is connected to the output shaft of the horizontally arranged first driving motor 21, and the eccentric axis of the first eccentric wheel 221 is connected to the horizontally arranged first connecting rod 222. The first optical axis 223 is connected to the first connecting rod 222.

The first linear bearing 224 and the second linear bearing 225 are respectively sleeved on both ends of the first optical axis 223. The first linear bearing 224 is connected to the gantry-shaped first support frame 226 (one vertical plate is hidden in the figure), and the second linear bearing 225 is fixed below the fixed plate 14.

The first detection probe 23 is mounted at the upper end of the first optical axis 223 to connect with the plantar soft tissue. In this embodiment, the top plate 15 has a hole corresponding to the first detection probe 23, allowing the first detection probe 23, raised by the corresponding lifting mechanism 50, to pass through the hole and contact the plantar soft tissue placed on the top plate 15.

In this embodiment, the first detection probe 23 can be set as a vacuum composite suction probe or a rigid flat probe according to the subject's preference. When the first detection probe 23 is a vacuum suction probe, the vacuum generator achieves a certain pressure, causing the suction probe to adhere to the skin surface of the plantar soft tissue. When the detection probe is a rigid flat probe, the rigid flat surface of the probe is adhered to the skin surface of the plantar soft tissue using a biocompatible, easy-to-clean adhesive, thereby achieving contact between the first detection probe 23 and the plantar soft tissue.

The first tension-compression sensor 24 is connected between the first detection probe 23 and the first optical axis 223 to detect the pressure exerted by the plantar soft tissue on the first detection probe 23 in the vertical direction.

The first displacement sensor 25 is installed on the first support frame 226 fixed to the fixed plate 14 and is positioned beside the first optical axis 223 to detect the displacement of the first detection probe 23 during the testing process. In this embodiment, when measuring the normal pressure of the plantar soft tissue, the vertical displacement amplitude range of the first detection probe 23 is ±5 mm.

The lifting mechanism 50 corresponding to the vertical reciprocating stress-strain testing unit 20 includes a driving component 51, a Z-axis screw slider module 52, and a fixing piece 53.

The vertically arranged driving component 51 is connected to the screw of the Z-axis screw slider module 52. The lifting mechanism 50 drives the slider of the Z-axis screw slider module 52 to move through the driving component 51, thereby driving the first driving motor 21 connected to the slider of the Z-axis screw slider module 52 through the fixing piece 53 to move up and down in the vertical direction, and thus the first detection probe 23 moves up and down in the vertical direction.

Figure 4:
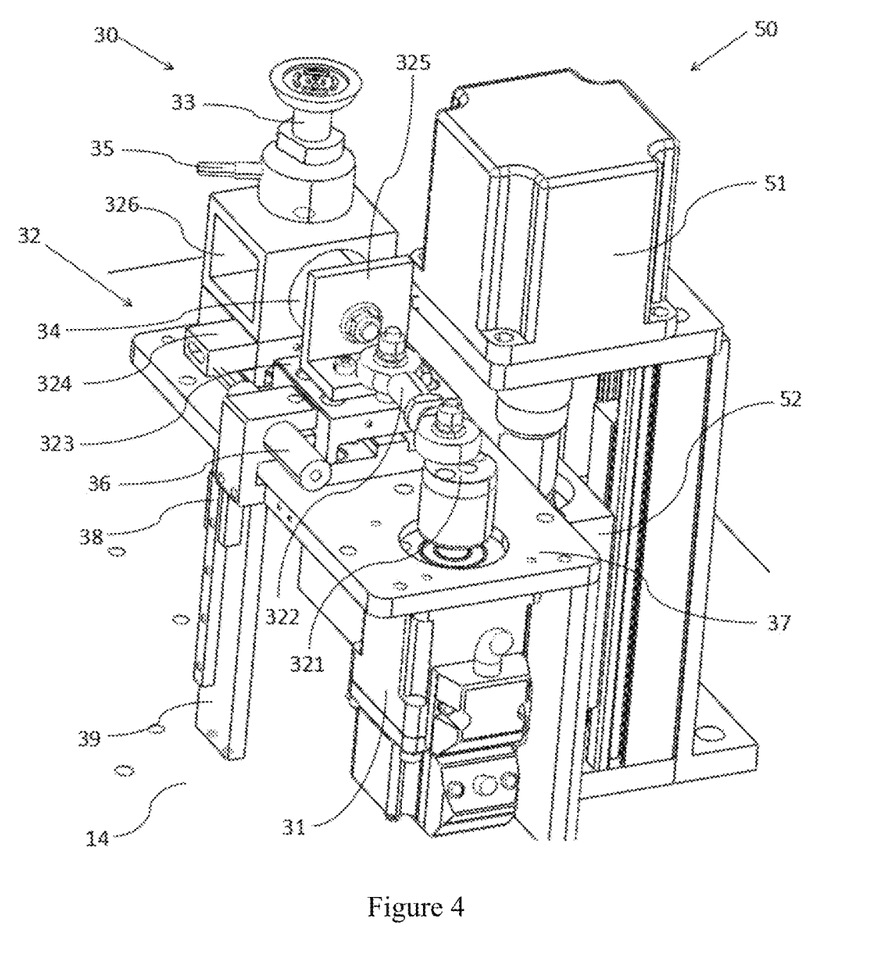
FIG. 4 is a structural diagram of the shear stress-strain testing unit and the corresponding lifting mechanism according to an embodiment of the present invention.

FIG. 4 shows a structural diagram of the shear stress-strain testing unit and the corresponding lifting mechanism according to an embodiment of the present invention.

As shown in FIG. 4, the shear stress-strain testing unit 30 is mounted on the testing table 10 and is used to apply transverse shear stresses to the plantar soft tissues and measure them. It includes a second driving motor 31, a second rotary-to-linear motion mechanism 32, a second detection probe 33, a second tension-compression sensor 34, a third tension-compression sensor 35, a second displacement sensor 36, a second support frame 37, a fixed guide rail 38, and a vertical fixed plate 39.

The second driving motor 31 is fixedly connected to the horizontal plate of the gantry-shaped second support frame 37 (one vertical plate is hidden in the figure).

The second rotary-to-linear motion mechanism 32 converts the rotational motion output by the second driving motor 31 into horizontal linear reciprocating motion to drive the second detection probe 33. It includes a second eccentric wheel 321, a connecting shaft 322, a second linear guide rail 323, a third linear guide rail 324, an L-shaped plate 325, and a first square connecting piece 326.

The center of the second eccentric wheel 321 is connected to the output shaft of the vertically arranged second driving motor 31. One end of the connecting shaft 322 is fixed to the edge of the second eccentric wheel 321, and the other end is connected to the slider of the second linear guide rail 323. The guide rail of the second linear guide rail 323 is fixed to the horizontal plate of the second support frame 37. The slider of the second linear guide rail 323 is connected to one end of the second tension-compression sensor 34 through the L-shaped plate 325, and the other end of the second tension-compression sensor 34 is connected to the side of the first square connecting piece 326. The upper end of the first square connecting piece 326, the third tension-compression sensor 35, and the second detection probe 33 are connected sequentially. The lower end of the first square connecting piece 326 is connected to the slider of the third linear guide rail 324. The guide rail of the third linear guide rail 324 is fixed to the horizontal plate of the second support frame 37.

The second detection probe 33 is used to connect with the plantar soft tissue. In this embodiment, the contact method and connection method of the second detection probe 33 with the plantar soft tissue are the same as those of the first detection probe 23, and will not be repeated here.

In this embodiment, the second driving motor 31 drives the third tension-compression sensor 35 to move laterally along the guide rail direction of the second linear guide rail, thereby detecting the force exerted on the second detection probe 33 in the transverse shear direction after contacting the plantar soft tissue.

The third tension-compression sensor 35 is used to detect the pressure exerted by the plantar soft tissue on the second detection probe 33 in the vertical direction.

The second displacement sensor 34 is arranged beside the slider of the second linear guide rail 323 to detect the displacement of the second detection probe 33 during the testing process. In this embodiment, when measuring the shear force of the plantar soft tissue, the tangential displacement amplitude range of the second detection probe 33 is ±5 mm.

The second support frame 37 (one vertical plate is hidden in the figure) is connected to the guide rail of the fixed guide rail 38. The slider of the fixed guide rail 38 is connected to the vertical fixed plate 39, which is fixed on the fixed plate 14.

The lifting mechanism 50 corresponding to the shear stress-strain testing unit 30 also includes a driving component 51 and a Z-axis screw slider module 52.

The vertically arranged driving component 51 is connected to the screw of the Z-axis screw slider module 52. The lifting mechanism 50 drives the slider of the Z-axis screw slider module 52 to move through the driving component 51, thereby driving the second support frame 37 connected to the slider of the Z-axis screw slider module 52 to move up and down in the vertical direction, so that the second detection probe 33 can move up and down in the vertical direction.

Figure 5:
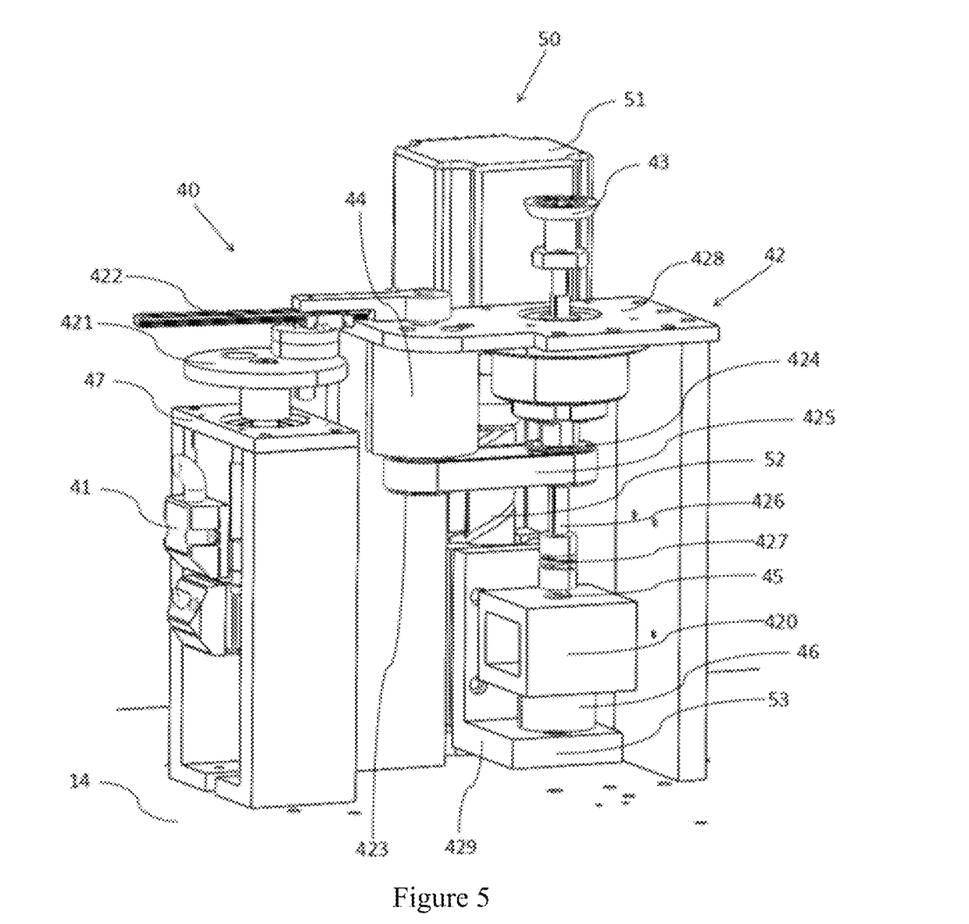
FIG. 5 is a structural diagram of the torque stress-strain testing unit and the corresponding lifting mechanism according to an embodiment of the present invention.

FIG. 5 shows a structural diagram of the torque stress-strain testing unit and the corresponding lifting mechanism according to an embodiment of the present invention.

As shown in FIG. 5, the torque stress-strain testing unit 40 is mounted on the testing table 10 and is used to apply torque to the plantar soft tissues and measure them. It includes a third driving motor 41, a rotary-to-torsion motion mechanism 42, a third detection probe 43, a torque sensor 44, an angle sensor 45, a fourth tension-compression sensor 46, and a third support frame 47.

The third driving motor 41 is fixed on the horizontal plate of the gantry-shaped third support frame 47, which is fixed on the fixed plate 14.

The rotary-to-torsion motion mechanism 42 converts the rotational motion output by the third driving motor 41 into horizontal torsional reciprocating motion to drive the third detection probe 43. It includes an eccentric turntable 421, a fourth linear guide rail 422, a first pulley 423, a second pulley 424, a synchronous belt 425, a torsion spline 426, a torsion coupling 427, a fourth support frame 428, an L-shaped fixing piece 429, and a second square connecting piece 420.

The center of the eccentric turntable 421 is connected to the output shaft of the vertically arranged third driving motor 41. The slider of the fourth linear guide rail 422 is mounted on the edge of the eccentric turntable 421. The guide rail of the fourth linear guide rail 422 is arranged horizontally and connected to one end of the vertically arranged torque sensor 44. The other end of the torque sensor 44 is connected to the first pulley 423. The first pulley 423 is connected to the second pulley 424 through the synchronous belt 425. The second pulley 424 is sleeved on the torsion spline 426.

The third detection probe 43, the torsion spline 426, the torsion coupling 427, and the angle sensor 45 are connected sequentially. The torsion bearing sleeved on the torsion spline 426 is fixed to the fourth support frame 428 (one plate is hidden in the figure) mounted on the fixed plate 14, ensuring the stability of the third detection probe 43 during the lifting process.

The third detection probe 43 is used to connect with the plantar soft tissue to be tested. The synchronous belt 425 drives the third detection probe 43 to perform reciprocating torsional motion. In this embodiment, the contact method and connection method of the third detection probe 43 with the plantar soft tissue are the same as those of the first detection probe 23, and will not be repeated here.

The torque sensor 44 synchronizes the torque applied by the third detection probe 43 on the plantar soft tissue through the synchronous belt 425, thereby detecting the torque exerted by the plantar soft tissue on the third detection probe 43.

The angle sensor 45 is arranged inside the second square connecting piece 420, with its upper end passing through the upper plane of the second square connecting piece 420 and connected to the torsion coupling 427, used to detect the rotation angle of the third detection probe 43 during the testing process. In this embodiment, when measuring the force-displacement of the torque of the plantar soft tissue, the rotation angle range is ±30°, and the cycle frequency does not exceed 100 Hz.

The upper end of the fourth tension-compression sensor 46 passes through the lower end of the second square connecting piece 420 and is arranged below the angle sensor 45 to detect the pressure exerted by the plantar soft tissue on the third detection probe 43 in the vertical direction. In this embodiment, when not in the testing state, the upper end of the fourth tension-compression sensor 46 does not contact the lower end of the angle sensor 45.

The lifting mechanism 50 corresponding to the torque stress-strain testing unit 40 also includes a driving component 51 and a Z-axis screw slider module 52.

The vertically arranged driving component 51 is connected to the screw of the Z-axis screw slider module 52. The lifting mechanism 50 drives the slider of the Z-axis screw slider module 52 to move through the driving component 51, thereby driving the fourth tension-compression sensor 46 connected to the slider of the Z-axis screw slider module 52 through the L-shaped fixing piece 429 to move up and down in the vertical direction. In this embodiment, when the fourth tension-compression sensor 46 rises to a certain height, it contacts the lower end of the angle sensor 45, driving the third detection probe 43 to move up and down in the vertical direction.

The vertical reciprocating stress-strain testing unit 20, the shear stress-strain testing unit 30, and the torque stress-strain testing unit 40 are arranged to face each other, with the first detection probe 23, the second detection probe 33, and the third detection probe 43 distributed at equal angular intervals on the same circumference. In this embodiment, the diameter of the circumference is set to 10±5 centimeters, resulting in a compact structure for the multi-dimensional broad-spectrum clinical in-situ testing equipment 100, facilitating portability and enabling the entire plantar surface to be placed at all angular directions for testing. This allows for dynamic force-displacement characteristic testing of normal pressure, shear force, and torque at any position on the plantar surface.

The following describes the use process of the multi-dimensional broad-spectrum clinical in-situ testing equipment 100.

The subject's foot is fixed on the top plate 15, and the plantar soft tissue area to be measured is pre-aligned through the hole in the top plate 15.

After pre-alignment of the plantar soft tissue area, the vertical reciprocating stress-strain testing unit 20, the shear stress-strain testing unit 30, and the torque stress-strain testing unit 40 corresponding lifting mechanisms 50 drive the vertical screw to move the slider of the Z-axis screw slider module 52 through the driving component 51, thereby raising the corresponding detection units connected to the slider of the Z-axis screw slider module 52 until the first detection probe 23, the second detection probe 33, and the third detection probe 43 respectively contact the plantar soft tissue, and the first tension-compression sensor 24, the third tension-compression sensor 35, and the fourth tension-compression sensor 46 show certain values, completing the lifting action of the corresponding lifting mechanisms 50. At this time, the detection probes are fixed to the skin surface of the corresponding plantar soft tissue through vacuum adsorption or adhesive, allowing the linkage motion to drive the plantar soft tissue to synchronously displace.

Subsequently, the detection stage begins. The vertical reciprocating stress-strain testing unit 20 applies vertical tensile and compressive stresses to the plantar soft tissue through the first driving motor 21 and detects and records the force and displacement through the first tension-compression sensor 24 and the first displacement sensor 25, respectively. The shear stress-strain testing unit 30 applies transverse shear stresses to the plantar soft tissue through the second driving motor 31 and detects and records the force and displacement through the second tension-compression sensor 34 and the second displacement sensor 36, respectively. The torque stress-strain testing unit 40 applies torque to the plantar soft tissue through the third driving motor 41 and detects and records the torque and rotation angle through the torque sensor 44 and the angle sensor 45, respectively. In this embodiment, the periodic data recorded are analyzed using the classical DMA method.

What is claimed is:

1. A multi-dimensional broad-spectrum clinical in-situ testing equipment for evaluating mechanical properties of a plantar soft tissue, comprising:
   a testing table with a designated testing area corresponding to a sole of a foot;
   a vertical reciprocating stress-strain testing unit mounted on the testing table, capable of applying vertical tensile and compressive stresses to the plantar soft tissue and measuring vertical reciprocating stress-strain responses;
   a shear stress-strain testing unit, also mounted on the testing table, for applying transverse shear stresses to the plantar soft tissue and measuring shear stress-strain responses;
   a torque stress-strain testing unit, positioned on the testing table, for applying torque to the plantar soft tissue and measuring torque stress-strain responses; and
   a lifting mechanism that facilitates a vertical movement of the vertical reciprocating stress-strain testing unit, the shear stress-strain testing unit, and the torque stress-strain testing unit;
   wherein the vertical reciprocating stress-strain testing unit, the shear stress-strain testing unit, and the torque stress-strain testing unit are arranged to face each other;
   each of the vertical reciprocating stress-strain testing unit, the shear stress-strain testing unit, and the torque stress-strain testing unit includes a detection head, wherein the detection heads of the vertical reciprocating stress-strain testing unit, the shear stress-strain testing unit, and the torque stress-strain testing unit are distributed at equal angular intervals on the same circumference;
   the shear stress-strain testing unit comprises a second driving motor, a second rotary-to-linear motion mechanism, a second detection probe, a second tension-compression sensor, a third tension-compression sensor, and a second displacement sensor;
   the second rotary-to-linear motion mechanism converts a rotational motion output by the second driving motor into horizontal linear reciprocating motion to drive the second detection probe, which is the detection head of the shear stress-strain testing unit and is connected to the plantar soft tissue;
the second tension-compression sensor detects a pressure applied to the second detection probe by the plantar soft tissue in a transverse shear direction;
the third tension-compression sensor detects a pressure applied to the second detection probe by the plantar soft tissue in a vertical direction;
the second displacement sensor detects a displacement of the second detection probe during a testing process;
the second rotary-to-linear motion mechanism comprises a second eccentric wheel, a connecting shaft, a second linear guide rail, a third linear guide rail, an L-shaped plate, and a first square connecting piece;
a center of the second eccentric wheel is connected to an output shaft of the second driving motor that is vertically arranged;
an end of the connecting shaft is fixed to an edge of the second eccentric wheel, and the other end of the connecting shaft is connected to a slider of the second linear guide rail;
an end of the second tension-compression sensor is connected to the slider of the second linear guide rail through the L-shaped plate, and the other end the second tension-compression sensor is connected to a side of the first square connecting piece;
the second detection probe, the third tension-compression sensor, the first square connecting piece, and a slider of the third linear guide rail are connected sequentially;
the second displacement sensor is arranged beside the slider of the second linear guide rail;
the vertical reciprocating stress-strain testing unit comprises a first driving motor, a first rotary-to-linear motion mechanism, a first detection probe, a first tension-compression sensor, and a first displacement sensor;
the first rotary-to-linear motion mechanism converts a rotational motion output by the first driving motor into vertical linear reciprocating motion to drive the first detection probe, which is the detection head of the vertical reciprocating stress-strain testing unit and is connected to the plantar soft tissue;
the first tension-compression sensor detects a pressure applied to the first detection probe by the plantar soft tissue in the vertical direction;
the first displacement sensor detects a displacement of the first detection probe during the testing process;
the first rotary-to-linear motion mechanism comprises a first eccentric wheel, a first connecting rod, a first optical axis, a first linear bearing, a second linear bearing, and a first support frame;
a rotation center axis of the first eccentric wheel is connected to an output shaft of the first driving motor that is horizontally arranged, and an eccentric axis of the first eccentric wheel is connected to the first connecting rod that is horizontally arranged;
the first optical axis is connected to the first connecting rod;
the first linear bearing and the second linear bearing are respectively sleeved on both ends of the first optical axis, and the first linear bearing is connected to the first support frame;
the first detection probe is arranged at an upper end of the first optical axis;
the first tension-compression sensor is connected between the first detection probe and the first optical axis;
the first displacement sensor is installed on the first support frame and arranged beside the first optical axis;
the torque stress-strain testing unit comprises a third driving motor, a rotary-to-torsion motion mechanism, a third detection probe, a torque sensor, an angle sensor, and a fourth tension-compression sensor;
the rotary-to-torsion motion mechanism converts a rotational motion output by the third driving motor into horizontal torsional reciprocating motion to drive the third detection probe, which is the detection head of the torque stress-strain testing unit and is connected to the plantar soft tissue to be tested;
the torque sensor detects a torque applied to the third detection probe by the plantar soft tissue;
the angle sensor detects a rotation angle of the third detection probe during the testing process;
the fourth tension-compression sensor detects a pressure applied to the third detection probe by the plantar soft tissue in the vertical direction;
the rotary-to-torsion motion mechanism comprises an eccentric turntable, a fourth linear guide rail, a first pulley, a second pulley, a synchronous belt, a torsion spline, and a torsion coupling;
a center of the eccentric turntable is connected to an output shaft of the third driving motor that is vertically arranged;
a slider of the fourth linear guide rail is installed on an edge of the eccentric turntable;
a guide rail of the fourth linear guide rail is arranged horizontally and connected to an end of the torque sensor that is vertically arranged;
the other end of the torque sensor is connected to the first pulley;
the first pulley is connected to the second pulley through the synchronous belt;
the second pulley is sleeved on the torsion spline;
the third detection probe, the torsion spline, the torsion coupling, and the angle sensor are connected sequentially;
the fourth tension-compression sensor is arranged directly below the angle sensor;
the lifting mechanism comprises a driving component and a Z-axis screw slider module;
the driving component that is vertically arranged is connected to a screw of the Z-axis screw slider module; and
a slider of the Z-axis screw slider module is connected to and drives the vertical reciprocating stress-strain testing unit, the shear stress-strain testing unit, and the torque stress-strain testing unit to move up and down in the vertical direction.

2. The multi-dimensional broad-spectrum clinical in-situ testing equipment for evaluating the mechanical properties of the plantar soft tissue according to claim 1, wherein the testing table comprises a fixed plate, a damping sheet, and a base plate;
wherein the vertical reciprocating stress-strain testing unit, the shear stress-strain testing unit, and the torque stress-strain testing unit are mounted on the fixed plate; and wherein the damping sheet is installed between the fixed plate and the base plate.

3. The multi-dimensional broad-spectrum clinical in-situ testing equipment for evaluating the mechanical properties of the plantar soft tissue according to claim 1, wherein a diameter of the circumference on which the detection heads of the vertical reciprocating stress-strain testing unit, the shear stress-strain testing unit, and the torque stress-strain testing unit are distributed is 10±5 centimeters.

* * * * *